United States Patent [19]

Dilks, Jr.

[11] 4,357,235
[45] Nov. 2, 1982

[54] DRIVE FOR ROTATING SEAL

[75] Inventor: Charles H. Dilks, Jr., Newark, Del.

[73] Assignee: E. I. Du Pont de Nemours and Company, Wilmington, Del.

[21] Appl. No.: 125,854

[22] Filed: Feb. 29, 1980

[51] Int. Cl.$^3$ .............................................. B03B 5/00
[52] U.S. Cl. .................................. 209/155; 233/1 A; 233/27
[58] Field of Search ................... 209/1, 155, 208, 444, 209/453, 11; 55/67, 81; 73/432 PS, 23.1; 210/198 C, 72; 233/1 R, 1 A, 1 D, 14 R, 23 R, 25, 26, 27

[56] References Cited

U.S. PATENT DOCUMENTS

| | | | |
|---|---|---|---|
| 2,476,894 | 7/1949 | Mulheim | 74/574 |
| 2,878,992 | 3/1959 | Pickels et al. | 233/11 |
| 2,889,695 | 6/1959 | Moeller | 64/1 |
| 3,097,167 | 7/1963 | Beyerle | 233/23 |
| 4,011,972 | 3/1977 | Pederson et al. | 233/1 A |

FOREIGN PATENT DOCUMENTS

| | | | |
|---|---|---|---|
| 1910576 | 9/1970 | Fed. Rep. of Germany | 233/1 A |
| 925677 | 5/1963 | United Kingdom | 233/1 A |

OTHER PUBLICATIONS

Sorvall RC-5B, Advertizing Brochure of Du Pont Company, Biomedical Products Division, Newtown, Conn.

SZ-14 Reorienting Density Gradient Zonal Rotor, Technical Brochure of Ivan Sorvall, Inc., Norwalk, Conn. 3/71.

*Primary Examiner*—Ralph J. Hill

[57] ABSTRACT

A long, thin annular belt-like channel can be used in sedimentation field flow fractionation. A rotating seal is required to couple fluids to the channel inlet and from the channel outlet. A flexible shaft is used to drive the rotating seal and thereby decouple rotor vibrations, which cause can leakage, from the rotating seal.

2 Claims, 4 Drawing Figures

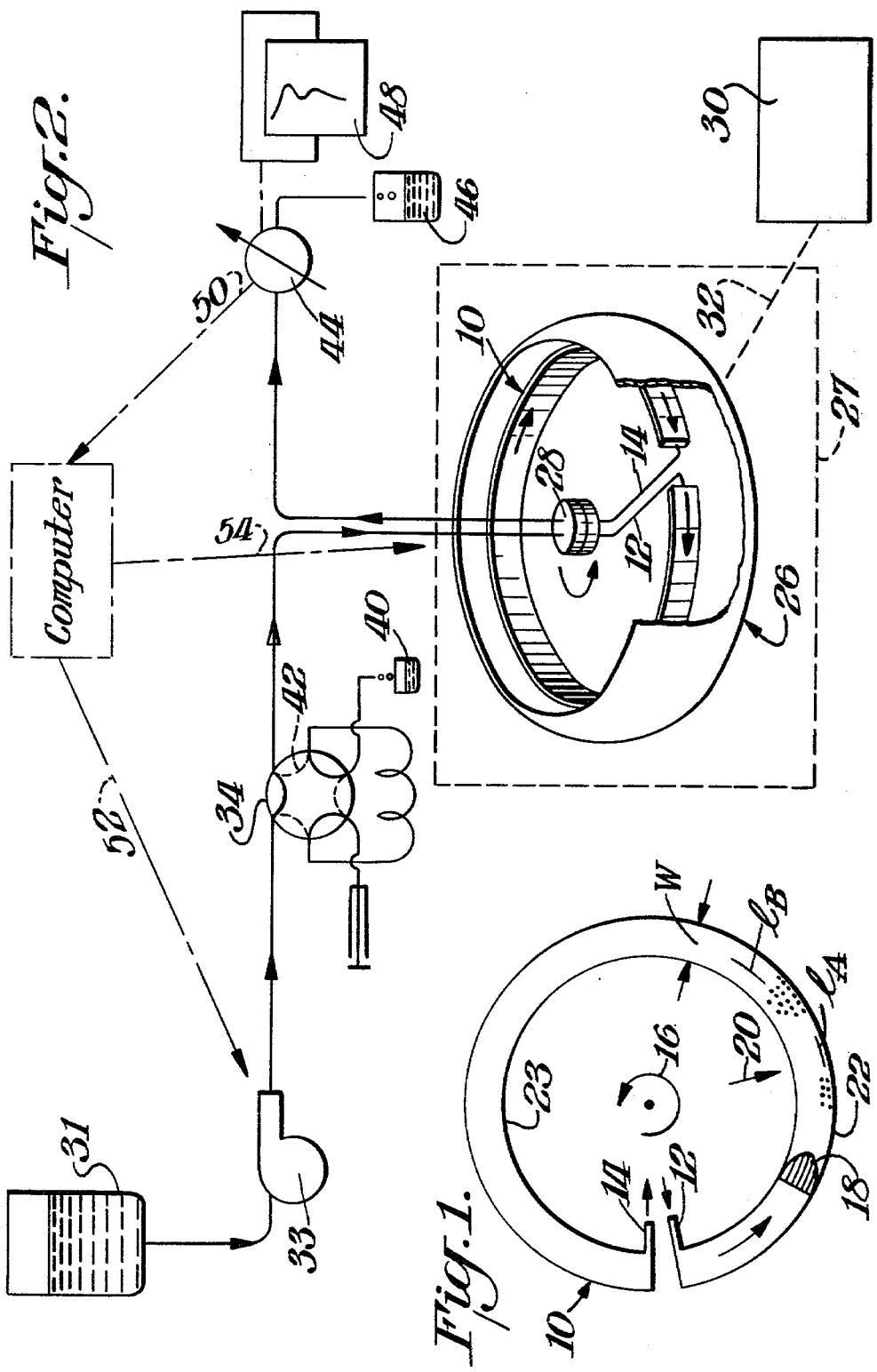

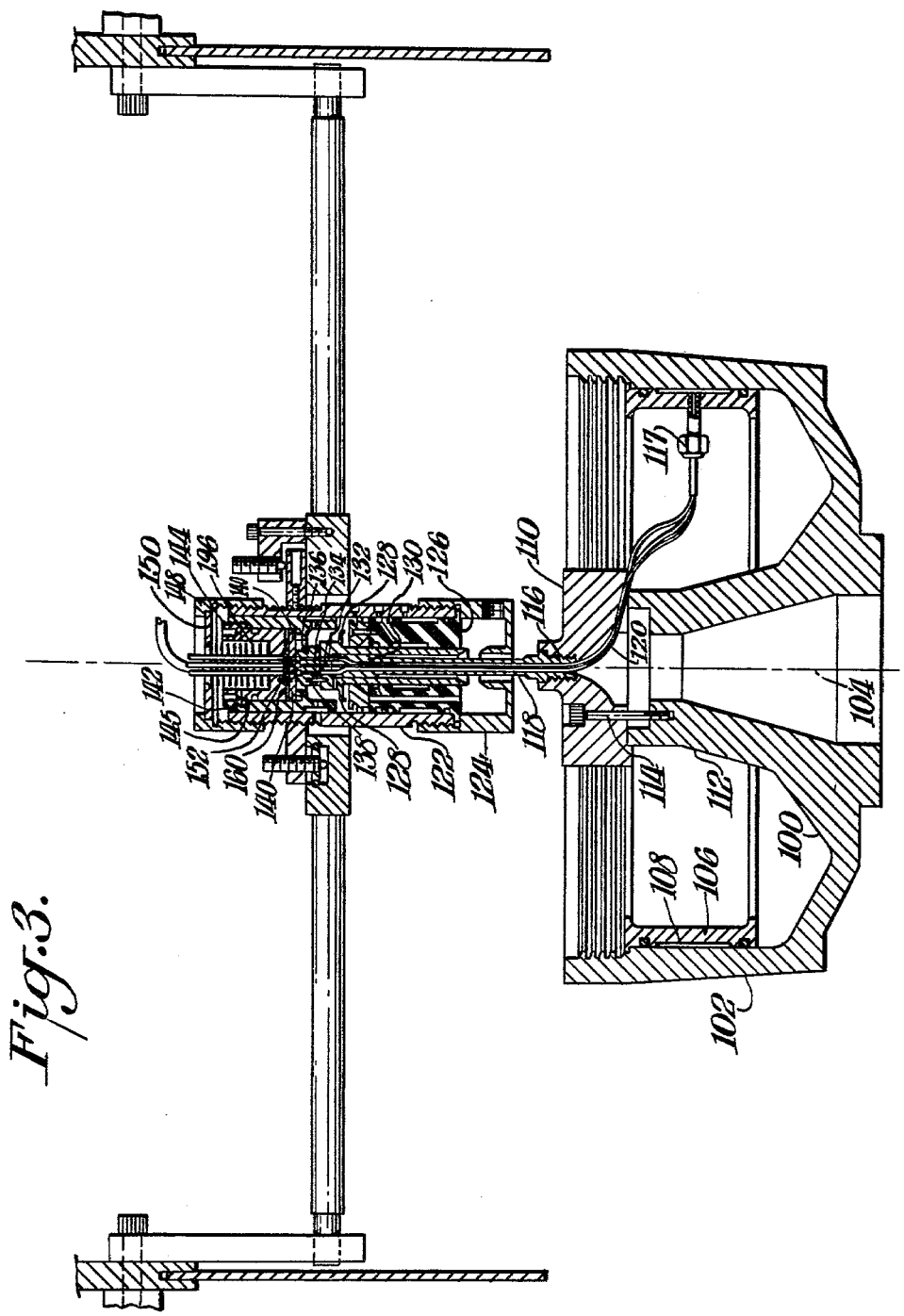

DRIVE FOR ROTATING SEAL

BACKGROUND OF THE INVENTION

Sedimentation field flow fractionation is a versatile technique for the high resolution separation of a wide variety of particulates suspended in a fluid medium. The particulates include macromolecules in the $10^5$ to the $10^{13}$ molecular weight (0.001 to 1 $\mu$m) range, colloids, particles, micelles, organelles and the like. The technique is more clearly described and more explicitly described in U.S. Pat. No. 3,449,938, issued June 17, 1969 to John C. Giddings and U.S. Pat. No. 3,523,610, issued Aug. 11, 1970 to Edward M. Purcell and Howard C. Berg.

Field flow fractionation is the result of the differential migration rate of components in a carrier or mobile phase in a manner similar to that experienced in chromatography. However, in field flow fractionation there is no separate stationary phase as is in the case of chromatography. Sample retention is caused by the redistribution of sample components between the fast to the slow moving strata within the mobile phase. Thus, particulates elute more slowly than the solvent front. Typically a field flow fractionation channel consisting of two closely spaced parallel surfaces is used. A mobile phase is caused to flow continuously through the gap between the surfaces. Because of the narrowness of this gap or channel (typically 0.025 centimeters (cm)), the mobile phase flow is laminar with a characteristic parabolic velocity profile. The flow velocity is the highest at the middle of the channel and the lowest near the two channel surfaces.

An external force field of some type (the force fields include gravitational, thermal, electrical, fluid cross-flow and others described variously by Giddings and Berg and Purcell), is applied transversely (perpendicular) to the channel surfaces or walls. This force field pushes the sample components in the direction of the slower moving liquid strata near the outer wall. The buildup of sample concentration near the wall, however, is resisted by the normal diffusion of the particulates in a direction opposite to the force field. This results in a dynamic layer of component particles, each component with an exponential-concentration profile. The extent of retention is determined by the time-average position of the particulates within the concentration profile which is a function of the balance between the applied field strength and the opposing tendency of particles to diffuse.

In sedimentation field flow fractionation, use is made of a centrifuge to establish the force field required for the separation. For this purpose, a long, thin annular belt-like channel is made to rotate within a centrifuge. The resultant centrifugal force causes components of higher density than the mobile phase to settle toward the outer wall of the channel. For equal particle density, because their of higher diffusion rate, smaller particulates will accumulate into a thicker layer against the outer wall than will larger particles. On the average, therefore, larger particulates are forced closer to the outer wall.

If now the fluid medium, which may be termed a mobile phase or solvent, is fed continuously in one end of the channel, it carries the sample components through the channel for later detection at the outlet of the channel. Because of the shape of the laminar velocity profile within the channel and the placement of particulates in that profile, solvent flow causes smaller particulates to elute first, followed by a continuous elution of sample components in the order of ascending particulate mass.

A rotating seal is used to couple the fluid medium or solvents in and out of the flow channel. Unfortunately, conventional rotating seals that have been designed for use in continuous flow type centrifuges have proven inadequate. The problems encountered with such seals are caused primarily by the fact that with the annular channels used in field flow fractionation, relatively large weights are placed at large radial distances. Under these conditions it is relatively difficult to achieve the degree of balance needed to reduce vibrations to an acceptable level to allow the use of conventional rotating seals.

This vibration problem is exacerbated when split ring type channels (described in an application Ser. No. 125,855, filed Feb. 29, 1980, entitled "Rotor for Sedimentation Field Flow Fractionation," by John Wallace Grant) are used since split ring channels tend to create some weight inbalance. With such vibrations, leakage in the seal face occurs and also seal wear becomes significant. The result is a short seal life and a sometimes severe limitation on rotor speeds that can be used. One solution to this problem is to mount the rotating seal as an independently floating face seal. While workable, such solutions have proven expensive and generally fail to produce what may be deemed a practical working system.

Thin metal tubes have been tried but also have proven unsatisfactory since they become subject to a "set" with the tubes becoming crimped resulting in even larger vibrations imposed upon the connected rotating seal assembly. This results in unacceptable seal leaks and relatively short seal lifetimes.

SUMMARY OF THE INVENTION

The invention described herein is used in an apparatus for separating particulates suspended in a fluid medium according to their effective masses, the apparatus having a housing, an annular cylindrical channel with a cylinder axis, rotor means mounted in the housing for rotating the channel about the axis, pump means and a rotating seal for passing the fluid medium circumferentially through the channel, means for introducing the particulates into the medium for passage through the channel and means connected to the effluent of the channel for detecting the presence of the particulates. The particulate-separating apparatus is improved in accordance with this invention by supporting the rotating seal means on the rotor means by a flexible hollow drive shaft.

In one embodiment of the invention, flexible narrow bore tubing is housed within the hollow shaft and interconnects the rotating seal with the inlet and outlet of the flow channel. In this manner torque for the drive of the seal is provided by the flexible shaft, and fluids are coupled through relatively low tensile strength tubing which does not transmit unwanted vibrations to the seal. The hollow shaft is selected from a plastic material having a stiffness sufficient to drive the rotating seal and a flexibility sufficient to substantially decouple the rotating seal from vibrations of the rotor.

BRIEF DESCRIPTION OF THE DRAWINGS

Further advantages and features of this invention will become apparent from the following description wherein:

FIG. 1 is a simplified schematic representation of the sedimentation field flow fractionation technique;

FIG. 2 is a partially schematic, partially pictorial representation of a particle separation apparatus constructed in accordance with this invention;

FIG. 3 is an elevation view in cross section of the rotating seal using a flexible, hollow drive shaft constructed in accordance with this invention.

DETAILED DESCRIPTION OF THE PREFERRED EMBODIMENT

Figure 4:
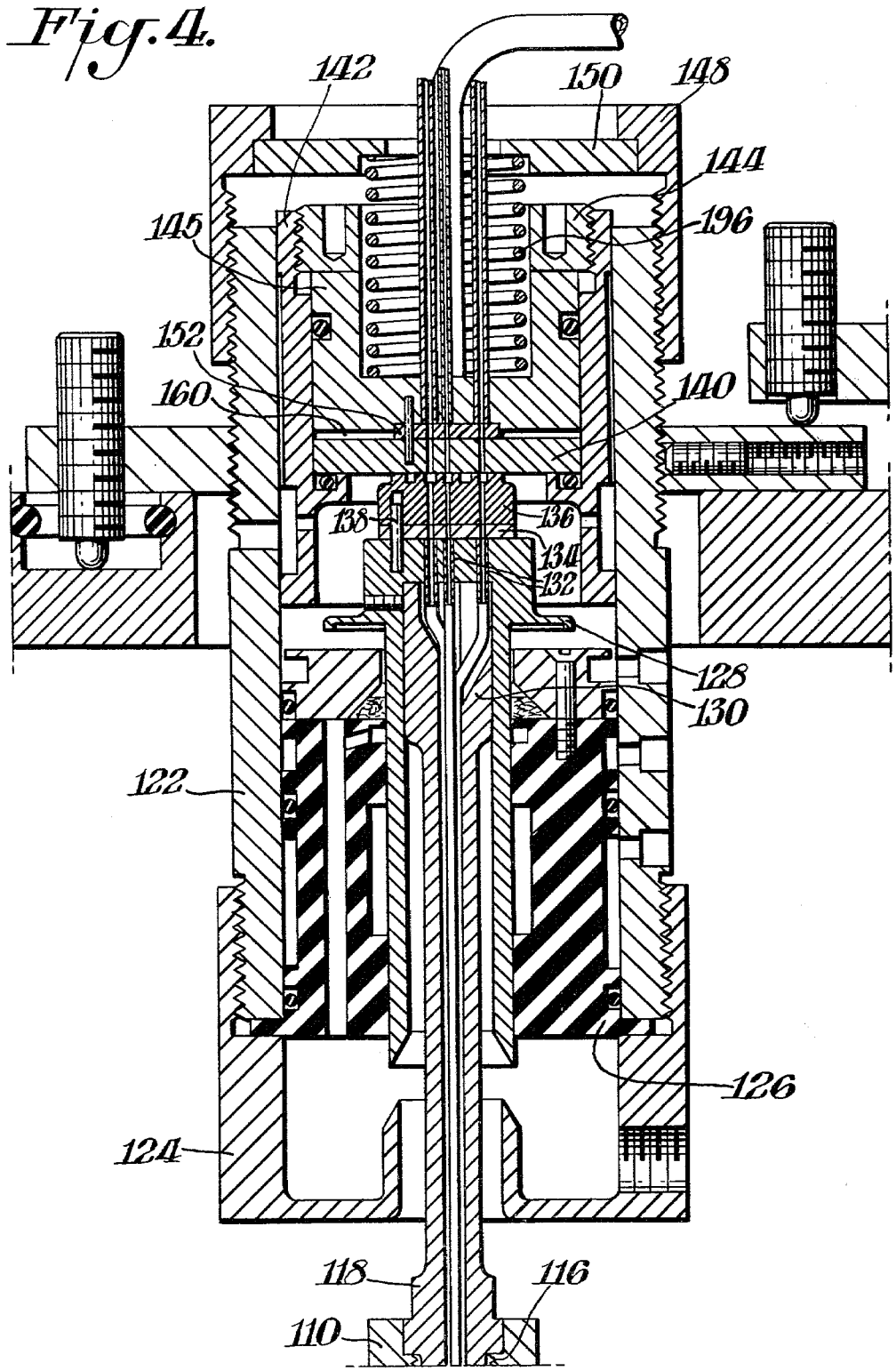
FIG. 4 is an enlarged cross sectional view of the rotating seal assembly of FIG. 3.

The principles of operation of a typical sedimentation field flow fractionation apparatus with which this invention may find use are perhaps more easily understood with reference to FIGS. 1 and 2. In FIG. 1 there may be seen an annular ringlike (alternatively, belt-like or ribbonlike) channel 10 having a relatively small thickness (in the radial dimension) designated W. The channel has an inlet 12 in which the fluid medium (hereinafter referred to as the mobile phase, liquid or simply fluid) is introduced together with, at some point in time, a small sample of a particulate to be fractionated, and an outlet 14. The annular channel is spun in either direction. For purposes of illustration the channel is illustrated as being rotated in a counterclockwise direction denoted by the arrow 16. Typically, the thickness of these channels may be in the order of magnitude of 0.025 cm; actually, the smaller the channel thickness, the greater rate at which separations can be achieved.

In any event, because of the thin channel, fluid flow is laminar and assumes a parabolic flow velocity profile across the channel thickness, as denoted by the reference numeral 18. The channel 10 is defined by an outer surface or wall 22 and an inner surface or wall 23. If now a radial centrifugal force field F, denoted by the arrow 20, is impressed transversely, that is at right angles to the channel, particulates are compressed into a dynamic cloud with an exponential concentration profile, whose average height or distance from the outer wall 22 is determined by the equilibrium between the average force exerted on each particulate by the field F and by opposing normal diffusion forces due to Brownian motion. Because the particulates are in constant motion at any given moment, any given particulate can be found at any distance from the wall. Over a long period of time compared to the diffusion time, every particulate in the cloud will have been at every different height from the wall many times. However, the average height from the wall of all of the individual particulates of a given mass over that time period will be the same. Thus, the average height of the particulates from the wall will depend on the mass of the particulates, larger particulates having an average height $1_A$ (FIG. 1) and that is less than that of smaller particulates $1_B$ (FIG. 1).

The fluid in the channel is now caused to flow at a uniform speed, so as to establish the parabolic profile of flow 18. In this laminar flow situation, the closer a liquid layer is to the wall, the slower it flows. During the interaction of the compressed cloud of particulates with the flowing fluid, sufficiently large particulates will interact with layers of fluid whose average speed will be less than the maximum for the entire liquid flow in the channel. These particulates then can be said to be retained or retarded by the field or to show a delayed elution in the field. This mechanism is described by Berg and Purcell in their article entitled "A Method For Separating According to Mass a Mixture of Macromolecules or Small Particles Suspended in a Fluid," I-Theory, by Howard C. Berg and Edward M. Purcell, Proceedings of the National Academy of Sciences, Vol. 58, No. 3, pages 862–869, September 1967.

According to Berg and Purcell, a mixture of macromolecules or small particulates suspended in a fluid may be separated according to mass, or more precisely what may be termed effective mass, that is, the mass of a particulate minus the mass of the fluid it displaces. If the particulates are suspended in the flowing fluid, they distribute themselves in equilibrium clouds whose scale heights, 1, depend on the effective masses, $m_e$, through the familiar relation $m_e a = kT$. In this relationship k is Boltzmann's constant, T is the absolute temperature, and a is the centrifugal acceleration. In view of this differential transit time of the particulates through a relatively long column or channel, the particulates become separated in time and elute at different times. Thus, as may be seen in FIG. 1, a cluster of relatively small particulates $1_B$ is ahead of and elutes first from the channel, whereas a cluster of larger, heavier particulates $1_A$ is noticed to be distributed more closely to the outer wall 22 and obviously being subjected to the slower moving components of the fluid flow will elute at a later point in time.

In FIG. 2 there is described a system for implementing SFFF. In this figure, the channel 10 may be disposed in a bowl-like or ringlike rotor 26 for support. The rotor 26 may be part of a conventional centrifuge, denoted by the dashed block 27, which includes a suitable centrifuge drive 30 of a known type operating through a suitable linkage 32, also a known type, which may be direct belt or gear drive. Although a bowl-like rotor is illustrated, it is to be understood that the channel 10 may be supported by rotation about its own cylinder axis by any suitable means such as a spider (not shown) or simple ring. The channel has a liquid or fluid inlet 12 and an outlet 14 which is coupled through a rotating seal 28, constructed in accordance with this invention, to the stationary apparatus which comprises the rest of the system. Thus the inlet fluid (or liquid) or mobile phase of the system is derived from suitable solvent reservoirs 30 which are coupled through a conventional pump 32 thence through a two-way, 6-port sampling valve 34, of conventional design, and through the rotating seal 28 to the inlet 12.

Samples whose particulates are to be separated are introduced into the flowing fluid stream by this conventional sampling valve 34 in which a sample loop 36 has either end connected to opposite ports of the valve 34 with a syringe 38 being coupled to an adjoining port. An exhaust receptacle 40 is coupled to the final port. When the sampling valve 34 is in the position illustrated by the solid lines, sample fluid may be introduced into the sample loop 36 with sample flowing through the sample loop to the exhaust receptacle 40. Fluid from the solvent reservoirs 30 in the meantime flows directly through the sample valve 34. When the sample valve 34 is changed to a second position, depicted by the dashed lines 42, the ports move one position such that the fluid stream from the reservoir 30 now flows through the sample loop 36 before flowing to the rotating seal 28.

Conversely, the syringe 38 is coupled directly to the exhaust reservoir 40. Thus the sample is carried by the fluid stream to the rotating seal 28.

The outlet line 14 from the channel 10 is coupled through the rotating seal 28 through the channel 10 and out through the rotating seal 28 to a conventional detector 44 and thence to an exhaust or collection receptacle 46. The detector may be any of the conventional types, such as an ultraviolet absorption or a light scattering detector. In any event, the analog electrical output of this detector may be connected as desired to a suitable recorder 48 of known type and in addition may be connected as denoted by the dashed line 50 to a suitable computer for analyzing this data. At the same time this system may be automated, if desired, by allowing the computer to control the operation of the pump 32 and also the operation of the centrifuge 28. Such control is depicted by the dashed lines 52 and 54, respectively.

The channel 10 preferably is constructed either of a split ring configuration as is described in said Grant application. These applications describe a split ring configuration for constructing an SFFF channel having a rectangular cross section and a relatively small (0.025 cm) radial thickness. Alternatively, of course, this channel may be constructed of a solid piece of material to have the rectangular configuration or may be formed of capillary tubing to as is described in an application Ser. No. 125,853, filed Feb. 29, 1980, entitled "Channel for Sedimentation Field Flow Fractionation" by Charles Heritage Dilks, Jr., Joseph Jack Kirkland and Wallace Wen-Chuan Yau.

Whatever the configuration and whether the flow channel is housed within a bowl-type rotor such as that depicted in FIG. 2 or is simply supported by a spider type configuration which is mounted to be driven on the conventional gyro drive of the centrifuge (not shown) is immaterial. Whatever the mounting for the channel, it is essential that the inlet and outlet of the channel be coupled through the rotating seal 28. This coupling is accomplished in accordance with the preferred embodiment of this invention in the manner depicted in FIG. 3.

There is seen in FIG. 3 a bowl-type centrifuge rotor 100 of generally conventional design (such as the TZ-28 rotor sold by E. I. du Pont de Nemours and Company, Wilmington, Del.), but modified to accommodate and form a field flow fractionation channel. For this purpose the verticle side wall 102 of the rotor has its inside surface formed with a flat portion, i.e., a portion parallel to the spin axis 104 an inner split ring 106 of the type described in said copending Grant application. Since this ring does not form a part of this invention and is only described to provide a complete disclosure, it need not be described in detail. Suffice it to say that the radially outer wall of the inner ring 106 is formed to have an outer groove which defines a thin channel 108. A disc-like bowl connector 110 is mounted on the raised center portion 112 of the bowl rotor as by a screw 114. The bowl connector 110 has a central bore 116 which is internally threaded to accommodate a torque tube or shaft 118 constructed in accordance with this invention.

This torque tube is hollow so as to accommodate, in this case, three flexible narrow bore tubing 120 which communicate with the inlet and outlet, respectively, of the flow channel 106. A suitable connector or tube coupling connector 117 of conventional design may be used for that purpose. This torque tube houses the flexible tubing 120 and couples them up through a rotating seal, also constructed in accordance with this invention, to the remainder of the SFFF system.

Although any rotating seal may be used, one that has proven particularly useful is that illustrated in FIG. 3. This rotating seal includes an annular seal bearing body 122 having a sump and body cap 124 secured as by threads to the lower end of a seal bearing body 122 that includes a bearing 126 of a suitable resilient material that is used for this purpose such as a self-lubricating silicone rubber or similar material. This bearing 126 houses a rotating seal spindle 128. The torque tube 118 has an enlarged upper end 130 positioned to rotate within the rotating seal spindle 128. This upper end 130 has axial passageways containing metal tubes 132 which are connected to the various tubes 120 and couple them through a gasket 134 to the rotating seal 136.

The rotating seal 136 is secured to the seal spindle 128 as by a pin 138. The upper rotating surface of the seal 136 has two annular grooves and a center hole formed therein in a conventional manner communicating with the various flow tubes 132. The rotating seal is constructed of any of the suitable plastic self-lubricating materials that are relatively chemically inert now used for such purpose.

The rotating seal 136 engages the lower face of a stationary seal 140. The stationary seal 140 is housed in the upper portion of the seal bearing body 122 and is supported by a stationary seal sleeve 142 which is slidingly positioned within the bearing body 122 and maintained with a downward thrust by a connector piece support 145, which houses a spring 196, and a keeper ring. In turn this spring is maintained in compression by a body cap 148 and a spring support plate or disc 150.

A gasket 152, having axial bores, positioned between the connector piece support 145 and the stationary seal disc, completes the assembly. If desired additional tubes for water cooling the stationary seal may be placed in an axial direction within the spring 146 passing through the connector piece support 145. Cooling fluid is permitted to flow through radial bores into the space 160 between the connector piece support 145 and the stationary seal disc 140. Suitable elastomeric gaskets may be used as indicated to complete the sealing.

In a preferred embodiment of the invention, the torque tube 118 provides the necessary strong flexible, hollow shaft between the rotor and the rotating seal to effectively decouple the face of the rotating seal from the rotor so that vibrations are not transmitted thereto.

The torque tube 118 must have the ability to transmit torque to the rotating seal and yet have sufficient flexibility to accommodate to the seal, such that the face of the rotating seal 136 can remain in intimate contact with the stationary seal disc 140. The torque tube 118 must be relatively rigid at the lower end and yet be flexible and at the same time transmit torque at the other. The ratio of the cube of the length to its radius is proportional to the ratio of its modules of elasticity E to its tensile strength S. For metal this ratio typically is in the order or 300, which is too high, causing the metal to crimp and transmit vibrations as noted. For typical nylon type plastics, this ratio is in the order of 30, less by a factor of ten than that of metals. These lower ratios are preferred to achieve the decoupling objectives of this invention. Preferably a nylon shaft, sold under the trademark Zytol 101, (available from E. I. du Pont de Nemours and Company, Wilmington, Del.) may be used. This shaft having dimensions of approximately 0.20 OD by 0.086 ID by 1.95 inches long has proven satisfactory.

The rotor can be run at relatively high speeds (e.g., at least 20,000 rpm) with little vibration transmitted to the rotating seal even when the rotor has not been completely balanced. Furthermore, the rotating seal has a relatively long life.

Alternatively the torque tube may be made from any one of many flexible plastic materials having a high modulus. Other suitable plastic materials include an acetal resin sold under the trademark Delrin by E. I. de Pont de Nemours and Company, Wilmington, Del., fiberglass, and a plastic embedded with a material such as an aramid fiber, sold under the trademark Kevlar by E. I. du Pont de Nemours and Company, Wilmington, Del. Essentially the torque tube must be formed of a material that is sufficiently stiff to provide a drive for this seal assembly but sufficiently flexible to decouple the rotating seal from the movements of the rotor as noted above. It is also desirable that the shaft be chemically inert and resistant to the various solvents that typically are used in SFFF separations. Further, it should also should be able to be used over a relatively wide range of temperatures. It also should be easily machined into the proper configuration.

I claim:

1. An apparatus for separating particulates suspended in a fluid medium according to their effective masses, said apparatus having a housing, an annular cylindrical channel with a cylinder axis, rotor means mounted in said housing for rotating said channel about said axis, pump means and a rotating seal for passing said fluid medium circumferentially through said channel, means for introducing said particulates into said medium for passage through said channel and means connected to the effluent of said channel for detecting the presence of said particulates, the improvement wherein said rotating seal means is supported on said rotor means by a flexible shaft, said flexible shaft being selected of a plastic material having a stiffness sufficient to drive said rotating seal and a flexibility sufficient to substantially decouple said rotating seal from vibrations of said rotor, the ratio of the modulus of elasticity to the tensile strength of said plastic material being about 30, thereby to transmit torque to said rotating seal.

2. An apparatus of claim 1 wherein said shaft is nylon.

* * * * *